(12) United States Patent
Lazar

(10) Patent No.: US 8,319,613 B2
(45) Date of Patent: *Nov. 27, 2012

(54) SMART CAP WITH COMMUNICATION FUNCTION

(76) Inventor: Steven Lazar, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/007,997

(22) Filed: Jan. 17, 2011

(65) Prior Publication Data

US 2011/0119090 A1 May 19, 2011

Related U.S. Application Data

(63) Continuation-in-part of application No. 12/322,929, filed on Feb. 9, 2009.

(51) Int. Cl.
*G08B 1/00* (2006.01)
(52) U.S. Cl. .................................. 340/309.16; 700/240
(58) Field of Classification Search ............ 340/309.16; 221/9, 10, 15; 700/240
See application file for complete search history.

(56) References Cited

U.S. PATENT DOCUMENTS

| | | | |
|---|---|---|---|
| 7,028,723 B1 * | 4/2006 | Alouani et al. ................. | 141/83 |
| 7,269,476 B2 * | 9/2007 | Ratnakar ...................... | 700/236 |
| 7,339,457 B2 * | 3/2008 | Trochesset ................. | 340/309.7 |
| 7,705,734 B2 * | 4/2010 | Martinelli ................... | 340/572.8 |
| 2003/0200726 A1 * | 10/2003 | Rast ................................ | 53/443 |
| 2006/0071011 A1 * | 4/2006 | Varvarelis et al. ................ | 221/9 |
| 2006/0200726 A1 * | 9/2006 | Gittins et al. ................. | 714/763 |
| 2006/0220818 A1 * | 10/2006 | Trochesset ..................... | 340/457 |
| 2007/0016443 A1 * | 1/2007 | Wachman et al. ................. | 705/2 |
| 2008/0027291 A1 * | 1/2008 | Williams-Hartman ........ | 600/300 |
| 2008/0056556 A1 * | 3/2008 | Eller et al. ..................... | 382/142 |
| 2009/0294521 A1 * | 12/2009 | de la Huerga ................. | 235/375 |

* cited by examiner

*Primary Examiner* — George Bugg
*Assistant Examiner* — Edny Labbees
(74) *Attorney, Agent, or Firm* — Israel Nissenbaum; Yitzy Nissenbaum

(57) ABSTRACT

A smart cap for a medical container for the containment of solid medications having unique indicia. The cap is provided with an optical scanner configured with at least one locally contained or external data base having general medication identification data and optionally patient-specific information to scan and identify the medication (and optionally the dosage, specific formulations, manufacturing source, etc.) and to record and correlate information regarding patient medication usage (scanning of a medication is generally considered indicative of actual patient taking of the medication). The cap further comprises communication elements configured to transmit/receive "usage" through scanning of a unit dosage of the medication, to an external data base such as the patient's cell phone and or computer (such as with blue tooth or RF communication) or via a telephone call or internet transmission to a data base of a pharmacy or physician or other health care provider.

20 Claims, 1 Drawing Sheet

SMART CAP WITH COMMUNICATION FUNCTION

This is a continuation in part of pending U.S. patent application Ser. No. 12/322,929, filed Feb. 9, 2009.

1 BACKGROUND OF THE INVENTION

A. Field of the Invention

Embodiments of the present invention, set forth herein, relate to a cap for a container, and more particularly, the embodiments of the present invention relate to a smart cap for a container used to dispense a medication and for automatically (a) verifying the taking of a medication by a patient and communication thereof to a pharmacy or other relevant entity, via an internet or other communication link or directly to the patient or caretaker to verify when and if a medication has been taken, (b) self-verifying the medication once the smart cap has been programmed for the medication so as to prevent improper dispensing thereof, (c) indicating and verifying the number of pills in the container, as well as the number remaining and the need for pharmacy restocking (d) indicating and verifying timing medication as prescribed (e) communicating relevant instructions and/or cautions in a language that the patient understands, as well as (f) providing other and different features and advantages flowing and/or derivable from these.

B. Description of Prior Art

Patients, especially the elderly, are prone to forget at times to take a medication or may not recall if they actually took it. This problem is aggravated with each additional medication that they are required to take See Improving Prescription Drug Container Labeling in the United States, A Health Literacy and Medication Safety Initiative, A White Paper Commissioned by the American College of Physicians Foundation.

Patients often fail to realize that they are out of a medication and must go without that medication until they can get a refill.

Patients are often non-compliant and fail to take medications of a prescribed basis.

Many patients from other countries are unable to understand English dosing instructions and/or cautions.

Errors can and do occur when physicians manuscript and/or when pharmacists read a prescription or dispense a medication to consumers. These risks have been increased by:

Increasing volume of prescriptions filled causing increased stress on physicians and on pharmacy staffs.

Pharmacies are often unable to determine actual medication usage and on many occasions have shortages of medications with unavailability to patients who need such medications.

Increasing use of poorly trained, overworked and/or mentally challenged pharmacy technicians.

Increasing additions of FDA-approved medications, many of which look alike or sound alike.

These mix-ups, have been documented and can cause great harm and even death to consumers.

More and more, consumers are becoming confused and even anxious that the medications they are taking are the ones prescribed by their physicians, because virtually every refill seems to contain a new and unfamiliar-looking generic form of a medication. This confusion is due to the fact that insurance plans frequently change their approved formulary—generic brands that they will pay for—usually approving a least expensive manufacturer at that particular time. In addition, more and more patients are seeing more than one physician (often as a result of patient insurance affiliation with doctors changing or the patients seeing different doctors for different illnesses). As a result, patients are now taking more and varied types of medications, quite often with one physician not knowing or being told (whether intentionally or unintentionally) of medications prescribed by another physician. Patients are thus seriously exposed to overmedication with duplicate prescriptions (particularly with different names of the same or similar medications) and increased risk of adverse drug interactions.

Even at the wholesale level, or in hospitals or in nursing homes, it is possible that a wrong medication is packaged in a large wholesale bottle or other container having a different label. It would be virtually impossible for the pharmacist to determine this mix-up. Additionally, on the retail and even consumer level, intentional and unintentional switching of medications among containers by the consumer or others can occur without current knowledge of the consumer.

Numerous innovations for medication verifying systems have been provided in the prior art which have been outlined in the parent of this application.

Numerous innovations for medication verifying systems have been provided in the prior art, some of which are being used. Furthermore, even though these innovations may be suitable for the specific individual purposes which they address, nevertheless, they would not be suitable for the purposes of the embodiments of the present invention as heretofore and hereafter described, namely, a smart cap for a container to dispense a medication and for automatically (a) self-verifying at least two (2) sides of the medication once the smart cap has been programmed for visually identifying the medication so as to prevent improper dispensing thereof, (b) indicating and verifying the number of pills in the container, (c) indicating and verifying timely, (for example daily/weekly/monthly) compliance for taking of the medication as prescribed, (d) communicating instructions and/or cautions to patients in a language(s) or vernacular(s) understandable to the patients, (e) verifying some or all of the foregoing by means of bar codes or other identifiers and/or communicating patient usage (or evidencing non-usage and non compliance) of a medication and ensuring a constantly available supply.

2. SUMMARY OF THE INVENTION

Thus, an object of the embodiments of the present invention is to provide a smart cap for a container to dispense a medication and for automatically recognizing the medication as a taken dose and communicating such usage to any or all of the patient or patient caretaker for verification of the taking of the medication, a dispensing pharmacy and/or to a prescribing physician for insuring proper stocking by pharmacies and patient reminders of renewing medications as well as unobtrusively monitoring patient compliance by a prescribing physician or other healthcare professional or caretaker. Optionally, the cap is configured for (a) self-verifying the medication once the smart cap has been automatically programmed for the medication so as to prevent improper dispensing thereof, (b) indicating and verifying the number of pills in the container, and (c) indicating and verifying timely compliance for medication as prescribed, (d) communicating instructions and/or cautions to patients. The cap is configured to accommodate use of bar codes and/or other indicia to participate in or verify or carry forward the teaching of this invention and to avoid the disadvantages of the prior art.

Briefly stated, another object of the embodiments of the present invention is to provide a smart cap for a container to automatically monitor usage and patient compliance as well as to dispense a medication and for automatically self-verifying the medication once the smart cap has been automatically programmed for the medication to prevent improper dispensing of the medication. The cap includes a first circuitry, a second circuitry, a third circuitry, and a first display. The first circuitry is disposed within the smart cap. The second circuitry automatically programs the first circuitry for the medication. The third circuitry is accessible within the smart cap, is in electrical communication with the first circuitry, and automatically scans the obverse and reverse sides of the medication, and (if necessary) other views of the medication, to provide a medication signal. The medication signal is sent from the third circuitry to the first circuitry to automatically self-verify the medication once the first circuitry has been programmed automatically by the second circuitry for the medication to provide a verification signal. The first display is visible on the smart cap, is in electrical communication with the first circuitry, and receives the verification signal from the first circuitry to prevent the improper dispensing of the medication.

In addition, or alternatively, the cap is provided with a short distance transmitter such as an RF transmitter or a blue tooth communication device to transmit by secondary means such as by telephone, particularly cell phones and smart phones or by WiFi or direct internet transmission, usage information of the medication on a pill by pill basis to a pharmacy and/or physician or other relevant entity or healthcare provider. The transmitter or communication device is uniquely programmed to the cap and the contained medication to provide specific usage by a patient of specific medication at specified times. For pharmacies, such information may be cumulated to maintain proper medication stock. Individual usage provides pharmacies with renewal requirement information and usage information transmitted directly or by the pharmacy to a treating physician monitoring compliance and, if necessary, indicates the need for corrective measures. Alternatively, the cell phone and particularly smart phone can be used to store the use information for direct retrieval by the patient or caretaker to ensure and keep track of taken medications.

The cap is programmed with software for communication and with cap-patient information. Such information preferably includes details of the medication including expiration date, dosage level, name of the drug (both common and trade name) as well as an indication if it is a generic version, the number of refills and the number of remaining refills on a prescription, whether there is duplication, prescribing doctor(s), pharmacist or other health professional, common side effects and interactions with other drugs and food, how and when to take the dosages and the ability to receive medication alerts from the internet. The information in the smart cap is preferably able to be locally stored and downloaded in addition to being configured for direct communication. Furthermore, it is also preferred that usage of the medication be entered, if appropriate, into an adverse reaction data base and patient history. The information stored in the data base of the smart cap is also preferably accessible for updating when called for or necessary. Such updating may be done by the patient or more preferably by the dispensing pharmacy, physician or other health professional aware of the changed information.

Another object of the embodiments is to generate a depiction of at least an obverse side and a converse side of the medication as part of the label generated from a label printer. Thusly a consumer can remove one of the units of the medications from its container and compare the unit visually with at least the obverse side and converse side thereof as depicted on the label.

Another object of the embodiments is to enable a pharmacist to self-verify a medication once the smart cap has been programmed for the medication so as to check inter alia the programming. Self verifying of the medication, most particularly its appearance, is available to the pharmacist at the time of placing the medication into the container. The self verifying of the medication also is performable by the consumer when the medication is being withdrawn by the consumer from the container.

Another object of the embodiment is to enable scanning of other features of the medication besides obverse and converse sides thereof. Side views, end views perspective views and cross-sectional views and profiles can easily be seen according to well-known technology, even though the size, shape, lettering or writing on each pill/capsule is unique.

Another object of the embodiment is to facilitate use of bar codes on medications to facilitate identifications. Where medication surfaces are not suitable for bar coding, those surfaces could be covered by a suitable substance that is receptive to printing and retention of a bar code.

Another object of the embodiment is to have the label printer of the pharmacist also be provided with an optically based receptacle similar to that of the smart cap for viewing at least an obverse side and a converse side of a medication (usually a questionable or unknown one). The label printer can be provided with a data base of the physical descriptions of virtually all medications, with the data base being updated constantly. In a pharmacy, hospital, nursing home or the like, where hundreds of medications are being dispensed on a daily basis, and with many new ones (especially generic) being introduced frequently, the optically based receptacle for viewing a medication would save time, effort and possible medication waste in identifying a questionable or unknown medication by placing that medication into the optically based receptacle and displaying (for example on a liquid crystal diode) or otherwise, and/or issue a printout of the medication's name, manufacturer, country of origin, expiration date, cautions, instructions, etc.

Generally the present invention comprises a cap for a medical container or vial for the containment of solid medications in the form of pills, capsules and the like having unique indicia. The medication and optionally the contained dosage, specific formulation and manufacturing source is identifiable by means such as by optical identification of indicia unique to the medication. The unique indicia include visible characteristics including color, size, shape, inscriptions thereon, etc. The cap is provided with a recognition element such as an optical scanner configured with at least one locally contained or external data base having general medication identification data and optionally patient-specific information to scan and identify the medication (and optionally the dosage, specific formulations, manufacturing source, etc.) and to record and correlate information regarding patient medication usage (scanning of a medication is generally considered indicative of actual patient taking of the medication). The cap further comprises communication elements configured to transmit "usage" through scanning of a unit dosage of the medication, to an external data base such as the patient's cell phone and or computer (such as with blue tooth or RF communication). The consumer or patient is optionally provided with a detailed summary (such as a print out) of all prescribed medications from the data base with duplicate medications or those with adverse interactions being flagged. Alternatively, the smart cap communicates the information regarding duplication and/or adverse interactions to a pharmacy providing one of the medications or to a prescribing physician for contacting the patient or consumer.

The smart cap itself may also be programmed to directly reject a particular medication by a visual or auditory warning unless manually overridden. Similarly, alerts (e.g., based on market withdrawals and recalls or newly discovered side effects or drug interactions) or medication dosage changes regarding specific medications can be conveyed via the communication elements in the smart cap.

Actual use of a proper medication is assumed with the use scanning and such information is conveyed via a telephone call or internet transmission to a data base of a pharmacy or physician or other health care provider. Use of the transmitted data is as appropriate and as outlined above. The novel features considered characteristic of the embodiments of the present invention are set forth in the appended claims. The embodiments of the present invention themselves, however, both as to their construction and their method of operation together with additional objects and advantages thereof will be best understood from the following description of the specific embodiments when read and understood in connection with the accompanying drawing.

3. BRIEF DESCRIPTION OF THE DRAWING

The figures of the drawing are briefly described as follows:

FIG. 1 is a diagrammatic perspective view of the smart cap of an embodiment of the present invention for a container to dispense a medication and for automatically (a) self-verifying the medication once the smart cap has been automatically programmed for the medication so as to prevent improper dispensing of the medication, (b) indicating and verifying the number of pills in the container, (c) indicating and verifying via timely (daily/weekly/monthly) compliance for medication as prescribed; and (d) communicating instructions and/or cautions to patients.

DETAILED DESCRIPTION OF THE PREFERRED EMBODIMENT

A. General

Figure 1:
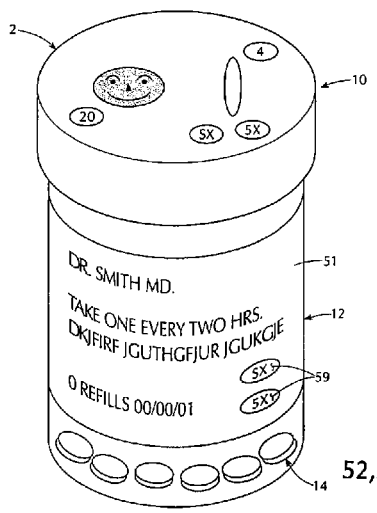

Referring now to the figures, in which like numerals indicate like parts, and particularly to FIG. 1, which is a diagrammatic perspective view of the smart cap of an embodiment of the present invention for a container containing a medication and for automatically self-verifying the medication once the smart cap has been automatically programmed for the medication so as to prevent improper dispensing of the medication, the smart cap of the embodiments of the present invention is shown generally at 10 for a container 12 containing a medication 14 and for automatically (a) self-verifying the medication 14 once the smart cap 10 has been automatically programmed for the medication 14 so as to prevent improper dispensing of the medication 14, (b) indicating and verifying the number of pills in the container, and (c) indicating and verifying daily/weekly/monthly compliance for medication as prescribed.

B. Configuration of the Smart Cap 10

Figure 2:
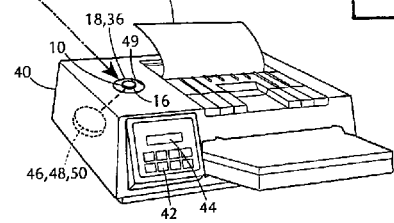
FIG. 2 is an exaggerated diagrammatic perspective view of the smart cap of an embodiment of the present invention identified by ARROW 2 in FIG. 1.
Figure 2:
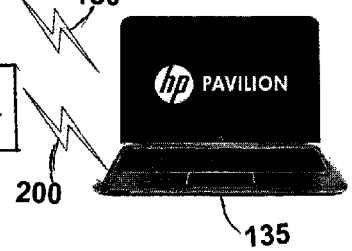

The configuration of the smart cap 10 can best be seen in FIG. 2, which is an exaggerated diagrammatic perspective view of the smart cap of an embodiment of the present invention identified by ARROW 2 in FIG. 1, and as such, will be discussed with reference thereto.

The smart cap, 10 comprises a first circuitry 16, a second circuitry 18, a third circuitry 20, a first display 22, a second display 24, a third display 26, and a fourth display 28. The first circuitry 16 is disposed within the smart cap 10. The second circuitry 18 automatically programs the first circuitry 16 for the medication 14. The third circuitry 20 is accessible within the smart cap 10, is in electrical communication with the first circuitry 16, and is for automatically scanning the obverse and reverse sides of the medication 14 so as to provide a medication signal 30. The medication signal 30 is sent from the third circuitry 20 to the first circuitry 16 for automatically self-verifying the medication 14 once the first circuitry 16 has been automatically programmed by the second circuitry 18 for the medication 14 so as to provide a verification signal 32. The first display 22 is visible on the smart cap 10, is in electrical communication with the first circuitry 16, and receives the verification signal 32 from the first circuitry 16 so as to prevent the improper dispensing of the medication 14. The second display 24 is visible on the smart cap 10, is in electrical communication with the first circuitry 16, and displays the obverse and reverse sides of the medication 14 inputted from the third circuitry 20 so as to prevent the improper dispensing of the medication 14. The third display 26 is visible on the smart cap 10, is in electrical communication with the first circuitry 16, and displays the frequency for taking the medication 14 once the first circuitry 16 has been automatically programmed by the second circuitry 18 for the medication 14. Audio means, well known in this art, can here issue instructions and/or cautions to the patient. The fourth display 28 is visible on the smart cap 10, is in electrical communication with the first circuitry 16, and displays the quantity of medication 14 in the container 12 starting with the prescribed quantity once the first circuitry 16 has been automatically programmed by the second circuitry 18 for the medication 14.

The first circuitry 16 comprises a sub-miniature chip 34 and a sub-miniature memory 36. The sub-miniature chip 34 of the first circuitry 16 is automatically programmed by the second circuitry 18 for the medication 14 and automatically self-verifies the medication 14 once the first circuitry 16 has been automatically programmed by the second circuitry 18 for the medication 14.

The second circuitry 18 comprises a sub-miniature programmer 36. The sub-miniature programmer 36 of the second circuitry 18 automatically programs the first circuitry 16 for the medication 14.

The third circuitry 20 comprises a sub-miniature scanner 38. The sub-miniature scanner 38 of the third circuitry 20 is for automatically scanning the obverse and reverse sides of the medication 14. A sample sub-miniature scanner 38 of the third circuitry 20 is the SC-5 type scanner that is manufactured by ELECTRO-OPTICAL PRODUCTS CORPORATION located at 88-65 76th Avenue, Glendale, N.Y. 11385, USA. See http://www.eopc.com/sc5.html. As used herein, optical scanners and scanning relate to any means by which visible characteristics are obtained or recordable in an format, such as but not limited to common pdf scanning and imaging and jpeg camera images.

The second circuitry 18 is disposed in a label printer 40. The label printer 40 comprises a keypad 42 and a printer display 44. The keypad 42 of the label printer 40 is for entering the medication 14, manufacturer/distributor of the medication 14, and patient information, and the printer display 44 of the label printer 36 is for displaying the medication 14, the manufacturer/distributor of the medication 14, and the patient information entered by the keypad 42 of the label printer 40.

The label printer 40 further comprises a fourth circuitry 46. The fourth circuitry 46 of the label printer 40 is in electrical communication with the second circuitry 18 and comprises a sub-miniature chip 48 and a sub-miniature memory 50 with a database of the medications 14 and the manufacturer/distributor of the medications 14 therein, allowing the keypad 42 of the label printer 40 to be used to enter the medication 14 and the consumer information to print on a label 51, while the second circuitry 18 simultaneously programs the first circuitry 16 with the medication 14, the manufacturer/distributor of the medication 14, the timely (daily/weekly/monthly) numerical frequency of the medication 14 prescribed, and the quantity of the medication 14 prescribed entered by the keypad 42 of the label printer 40 when the smart cap 10 is programmed by the second circuitry 18 by the second circuitry 18.

The label printer 40 further comprises a printer receptacle 48. The printer receptacle 48 in the label printer 40 has the second circuitry 18 thereat and holds the smart cap 10 while the second circuitry 18 programs the first circuitry 16.

The smart cap 10 further comprises a cap receptacle 53. The cap receptacle 53 of the smart cap 10 has the third circuitry 20 thereat and is a slot for holding the medication 14 while the third circuitry 20 scans the obverse and reverse sides of the medication 14.

The first display 22 of the smart cap 10 comprises a face 52. The face 52 of the first display 22 of the smart cap 10 receives the verification signal 32, and in response thereto, if the verification signal 32 is positive, then the face 52 of the first display 22 of the smart cap 10 assumes a smiling face 54, but if the verification signal 32 is negative, then the face 52 of the first display 22 of the smart cap 10 assumes a frowning face 56 so as to prevent the improper dispensing of the medication 14.

The smiling face 54 of the face 52 of the first display 22 of the smart cap 10 is illuminated green, while the frowning face 56 of the face 52 of the first display 22 of the smart cap 10 is illuminated red. Many other known positive/negative indicia could be substituted for the smiling/frowning faces.

The second display 24 of the smart cap 10 comprises a pair of medication sides 58. The pair of medication sides 58 of the second display 24 of the smart cap 10 depict the obverse and reverse sides of the medication 14 scanned by the third circuitry 20, which is then manually compared to a picture 59 of the obverse and reverse sides of the medication 14 on the label 51 (FIG. 1) entered by keypad 42 of the label printer 40 so as to be sure that the medication 14 being scanned by the third circuitry 20 is the prescribed medication 14.

The third display 26 of the smart cap 10 comprises a first digital counter 60. The first digital counter 60 of the third display 26 of the smart cap 10 depicts the numerical timely (daily/weekly/monthly) frequency of the medication 14 entered into the first circuitry 16 by the second circuitry 18 via the keypad 42 of the label printer 40 via the keypad 42 of the label printer 40 when the smart cap 10 is programmed by the second circuitry 18. It decreases by one each time the medication is placed in the cap receptacle so as to prevent improper (daily/weekly/monthly) dosage frequency of the medication 14.

The fourth display 28 of the smart cap 10 comprises a second digital counter 62. The second digital counter 62 of the fourth display 28 of the smart cap 10 depicts the quantity of the medication 14 entered into the first circuitry 16 by the second circuitry 18 via the keypad 42 of the label printer 40 via the keypad 42 of the label printer 40 when the smart cap 10 is programmed by the second circuitry 18, and decreases by one each time the medication 14 is placed in the cap receptacle and is scanned by the third circuitry 20 so as to alert when the medication 14 in the container 12 is running low.

C. Tabulations

| CIRCUITRY | FUNCTION |
|---|---|
| First Circuitry (16) | Main Processor |
| Second Circuitry (18) | Automatically programs the first circuitry (16) |
| Third Circuitry (20) | Automatically scans the obverse and reverse sides of the medication (14) |
| Fourth Circuitry (46) | Database of the medications (14) and the manufacturer/distributer of the medications (14) |
| DISPLAY | |
| First Display (22) | Depicts either a smiling green face (54) or a frowning red face (56) |
| Second Display (24) | Depicts the obverse and reverse sides of the medication (14) |
| Third Display (26) | Depicts the numerical daily/weekly/monthly frequency of the medication (14) |
| Fourth Display (28) | Depicts the quantity of the medication (14) remaining in the container. |

Figure 3:
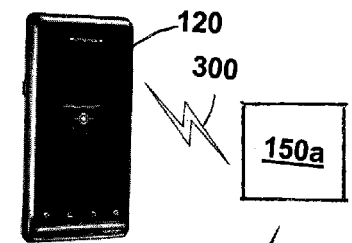
FIG. 3 is a schematic view of the smart cap being used to monitor usage and to communicate such usage to a pharmacy and/or a physician or other health care provider or directly to a data base accessible by the patient or caretaker.
Figure 3:
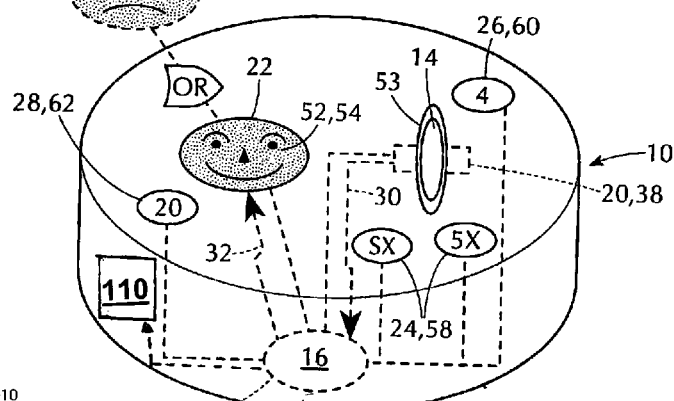

In the embodiment of FIG. 3, the smart cap 10 further includes a communication element 110 which receives scanned medication information from circuit 16. In this embodiment the medication or pill 14 is placed on smart cap 10 into cavity 53 for programmed wireless transmitter 110 to wirelessly transmit a usage signal of the medication.

The identity of the medication is determined and a patient identifying code is generated from circuit 16 when a pill 14 is removed from the container 12 and scanned. The smart cap 10 (programmed to effect transmission) sends a signal of patient use of medication via the transmitter 110 to a proximate phone 120 by bluetooth transmission 400 and telephone communication 300 directly to a pharmacy or physician/healthcare provider. Alternatively the transmitter 110 sends the signal by WiFi transmission 130 to a computer 135 for interne transmission 200 or direct (e.g. 3G and the like) transmission 200 via the internet to an e-mail or similar site of a pharmacy site 150 and/or physician site 160 whereby the usage is recorded with patient and medication identity and stamped with a time and date into a configured data base.

In a pharmacy database 150*a*, specific medication usage data is cumulated for stocking and disposal purposes and the usage is entered into a patient record file by both the pharmacy and physician. The pharmacy does a comparison with the amount of dispensed medication to determine renewal information with patient reminders.

The patient file data base 160*a* maintained by the treating physician is preprogrammed to generate an alarm if patient usage deviates significantly from the prescription data. As shown, the transmission is to any or all of the pharmacy database 150, a physician (or other health care provider) patient file data base 160, or to a data base 170 maintained by the patient or caretaker (keeping track of patient usage of a medication) on a smart phone 120 or local computer 135. As described, the patient can print out usage, medication information and the like to safeguard against excessive medication usage or incomplete compliance and the like.

The transmitter 110 may also be provided with a receiver function whereby outside sources such as the pharmacy, physician or even the FDA or other relevant agency can submit signals (shown as outside source 500) regarding the status of the medication, the need for renewal or warnings against medication usage (too much) or non compliance. A speaker (not shown) may allow for audio messages.

It will be understood that each of the elements described above or two or more together may also find a useful application in other types of constructions differing from the types described above.

While the embodiments of the present invention have been illustrated and described as embodied in a smart cap for a container to dispense a medication and for automatically (a) self-verifying the medication once the smart cap has been automatically programmed for the medication so as to prevent improper dispensing of the medication, (b) indicating and verifying the number of pills in the container, (c) indicating and verifying timely (daily/weekly/monthly) compliance for medication as prescribed and (d) communicating instructing instructions and/or cautions to patients in a language the patient understands. However, the invention is not limited to the details shown, since it will be understood that various omissions, modifications, substitutions, and changes in the forms and details of the embodiments of the present invention illustrated and their operation can be made by those skilled in the art without departing from the spirit of the embodiments of the present invention. For example, use of a container could be extrapolated to compartmental pill organizers, boxes, bags and other containers for dispensing such medications. The basic teaching herein could be adapted to liquid delivery systems to patients, such as drip stands and more complicated equipment. Other known audio and/or video components could be introduced hereto. And various warning apparatuses such as lights, annunciators, bells or the like could be included. Both of the sides of the medication pill should appear on a label on the container.

A smart cap according to this invention could easily be reused, being reprogrammed at a pharmacy. Patients could have his or hers own smart caps. Recirculation of the smart caps could be encouraged by refunds of deposits thereon. The invention touches many industrial, social and insurance facets in a very positive ways.

Without further analysis the foregoing will so fully reveal the gist of the embodiments of the present invention that others can by applying current knowledge readily adapt them for various kindred applications without omitting features that from the standpoint of prior art fairly constitute characteristics of the generic or specific aspects of the embodiments of the present invention.

What is claimed is:

1. A smart cap for a container dispensing a medication comprising:
   a) a medication scanning and recognition element configured to recognize the medication being scanned,
   b) the cap being configured to be programmed with the identity of medication which is property dispensed and is further configured to physically scan a medication being dispensed for use by a patient and to identify the medication being dispensed and to verify a match or a mismatch with the medication property dispensed and medication actually being dispensed; and
   c) a communication element configured to transmit information about scanned medication and its utilization by a patient to any or all of data bases maintained by a pharmacy, a physician or other health provider and the patient or patient caretaker.

2. The smart cap of claim 1, wherein the scanning and recognition element comprises an optical scanner electronically linked to a medication data base having medication identification information stored therein unique to different medications whereby the scanned medication is recognized and identified.

3. The smart cap of claim 1, wherein the communication element comprises a blue tooth receiver/transmitter device for communication with a proximate cell phone, smart phone or computer for transmission to any or all of the data bases.

4. The smart cap of claim 1, wherein the communication element comprises an RF transmitted for communication with a proximate cell phone, smart phone or computer for transmission to any or all of the data bases.

5. The smart cap of claim 1, the communication element comprises a WiFi element configured for direct internet transmission of usage information of the medication to any or all of the data bases.

6. The smart cap of claim 1, wherein the communication device is uniquely programmed to the cap and the contained medication to provide specific usage by a patient of specific medication at specified times.

7. The smart cap of claim 1, wherein the smart cap comprises:
   a) a first circuitry configured to be programmed with the identity of the medication which is properly dispense;
   b) a second circuitry configured to automatically program the first circuitry with said identity of the medication;
   c) a third circuitry configured to physically scan a medication being dispensed for use by a patient; and
   d) a display;
   wherein said first circuitry is disposed within said smart cap;
   wherein said third circuitry is accessible within said smart cap for physical scanning of the medication being dispensed;
   wherein said third circuitry is in electrical communication with said first circuitry;
   wherein third circuitry is configured for automatically scanning at least an observe side and a reverse side of the medication to thereby identify the medication being dispense to provide a medication signal;
   wherein the smart cap is programmed with software for communication and for containing and storing patient and related medication information with said information comprising details of the medication including at least one of expiration date, dosage level, common and trade name of the medication as well as an indication if it is a generic version, the number of refills and the number of remaining refills on a prescription, whether there is duplication, prescribing doctor or doctors or treating health profession, dispensing pharmacy, common side effects and interactions with other drugs and food, how and when to take the dosages and the ability to receive medication alerts from the internet, with information being visible on the display.

8. The smart cap of claim 7, wherein the smart cap is configured for communication into a remote adverse reaction data base and patient history.

9. The smart cap of claim 1, wherein the smart cap is adapted for use with a medical container or vial for the containment of solid medications in the form of pills or capsules having unique indicia wherein the identity of the medication and the contained dosage, specific formulation and manufacturing source is identifiable by means indicia unique to the medication comprising visible characteristics of at least color, size, shape, and inscriptions thereon, the smart cap being provided with an optical recognition scanner configured with at least one locally contained or external data base having general medication identification data and optionally patient-specific information to scan and identify the medication and to record and correlate information regarding patient medication usage as defined as unit dosage by the individual scanning of a pill or capsule, wherein the cap further comprises communication elements configured to transmit usage by the patient of the medication through scanning of a unit dosage of the medication, to an external data base in a patient's cell phone and or computer or to a data base of a pharmacy or physician or other health care provider.

10. The smart cap of claim 4, wherein at least one of the proximate cell phone, smart phone or computer comprise a database accessible for download by the patient or caretaker of medication and usage information.

11. The smart cap of claim 1, wherein the communication element further comprises a receiver element configured to receive information about the scanned medication and/or the patient.

12. A medication usage compliance and medication stocking system comprising the smart cap of claim 9 and at least one computer to which medication usage is transmitted with said at least one computer being accessible to at least one of a medication dispensing pharmacy and a prescribing physician or health care professional, wherein the computer is configured for the pharmacy to cumulate usage numbers to provide a basis for maintaining proper medication stock with individual usage information.

13. The medication usage compliance and medication stocking system of claim 12, wherein medication usage information is transmitted to computer accessible by a treating physician or health care professional to enable monitoring of patient compliance and, if necessary, indicating the need for corrective measures.

14. The medication usage compliance and medication stocking system of claim 12, wherein medication usage information is transmitted to computer accessible by the patient or patient caretaker to enable monitoring and verification of actual proper patient compliance.

15. The smart cap of claim 7, wherein the smart cap for a container dispensing a medication and for automatically self-verifying the medication once said smart cap has been automatically programmed for the medication so as to prevent improper dispensing of the medication, wherein the smart cap comprises first and second displays, wherein said second circuitry automatically programs said first circuitry for the medication;
  wherein said third circuitry is accessible within said smart cap; wherein said third circuitry is in electrical communication with said first circuitry; wherein said third circuitry is for automatically scanning at least an obverse side and a reverse side of the medication so as to provide a medication signal; wherein said medication signal is sent from said third circuitry to said first circuitry for automatically self-verifying the medication once said first circuitry has been automatically programmed by said second circuitry for the medication so as to provide a verification signal; wherein said first display is visible on said smart cap; wherein said first display is in electrical communication with said first circuitry; and wherein said first display receives said verification signal from said first circuitry so as to prevent the improper dispensing of the medication and wherein said second display is visible on said smart cap; wherein said second display is in electrical communication with said first circuitry; and wherein said second display displays the at least an obverse side and a reverse side of the medication inputted from said third circuitry so as to prevent the improper dispensing of the medication.

16. The cap of claim 15, further comprising a third display; wherein said third display is visible on said smart cap; wherein said third display is in electrical communication with said first circuitry; and wherein said third display displays frequency for taking the medication once said first circuitry has been automatically programmed by said second circuitry for the medication and recalibrates every time a pill is placed in the chamber.

17. The cap of claim 16, further comprising a fourth display; wherein said fourth display is visible on said smart cap; wherein said fourth display is in electrical communication with said first circuitry; and wherein said fourth display displays quantity of medication in the container starting with a prescribed quantity once said first circuitry has been automatically programmed by said second circuitry for the medication and recalibrates every time a pill is placed in the chamber.

18. The cap of claim 17, wherein said first circuitry comprises:
  a sub-miniature chip; and
  a sub-miniature memory;
  wherein said sub-miniature chip of said first circuitry is automatically programmed by said second circuitry for the medication and automatically self-verifies the medication once said first circuitry has been automatically programmed by said second circuitry for the medication.

19. The cap of claim 18, wherein said second circuitry comprises a sub-miniature programmer; and wherein said sub-miniature programmer of said second circuitry automatically programs said first circuitry for the medication.

20. The cap of claim 19, wherein said third circuitry comprises a sub-miniature scanner; and wherein said sub-miniature scanner of said third circuitry is for automatically scanning the obverse and reverse sides of the medication.

* * * * *